(12) United States Patent
Watanabe et al.

(10) Patent No.: US 9,962,491 B2
(45) Date of Patent: May 8, 2018

(54) SYRINGE WITH HANGING TAG

(71) Applicant: Terumo Kabushiki Kaisha, Tokyo (JP)

(72) Inventors: Eiji Watanabe, Kanagawa (JP); Eiji Kawamoto, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 36 days.

(21) Appl. No.: 14/430,515

(22) PCT Filed: Dec. 17, 2012

(86) PCT No.: PCT/JP2012/082650
§ 371 (c)(1),
(2) Date: Mar. 23, 2015

(87) PCT Pub. No.: WO2014/097366
PCT Pub. Date: Jun. 26, 2014

(65) Prior Publication Data
US 2015/0352286 A1    Dec. 10, 2015

(51) Int. Cl.
*A61M 5/178* (2006.01)
*A61M 5/20* (2006.01)
(Continued)

(52) U.S. Cl.
CPC ........ *A61M 5/2053* (2013.01); *A61M 5/1456* (2013.01); *A61M 5/3135* (2013.01);
(Continued)

(58) Field of Classification Search
CPC ...... A61M 2205/6609; A61M 2205/60; A61M 2005/3125; A61M 2005/3126;
(Continued)

(56) References Cited

U.S. PATENT DOCUMENTS 3,045,494 A    7/1962    Gerarde
3,391,694 A    7/1968    Spaeth
(Continued)

FOREIGN PATENT DOCUMENTS

JP    2003-225306 A    8/2003
JP    2005-182715       7/2005
(Continued)

OTHER PUBLICATIONS

International Search Report in PCT/JP2012/082650 dated Mar. 19, 2013.
(Continued)

*Primary Examiner* — Nathan R Price
*Assistant Examiner* — Gerald Landry, II
(74) *Attorney, Agent, or Firm* — Foley & Lardner LLP

(57) ABSTRACT

An indicating member for attachment to a syringe includes: a tag for indicating at least one administration condition of a liquid medicament, the tag including a through hole, an engaging section extending from the tag and configured to be attached to an engaging hole of a syringe, and a hanger that is provided with the tag via the through hole, and is configured to extend around and thereby hang from at least one of (i) a syringe barrel of the syringe, (ii) a nozzle of the syringe, (iii) a liquid medicament delivery tube attached to the syringe, and (iv) a syringe barrel nozzle connection section attached to the syringe.

7 Claims, 6 Drawing Sheets

(51) Int. Cl.
*A61M 5/31* (2006.01)
*A61M 5/145* (2006.01)

(52) U.S. Cl.
CPC . *A61M 2205/60* (2013.01); *A61M 2205/6009* (2013.01); *A61M 2205/6045* (2013.01); *A61M 2205/6063* (2013.01)

(58) Field of Classification Search
CPC .... A61M 5/3129; G09F 3/0288; G09F 3/005; G09F 3/00
USPC ....... 235/375; 283/70, 74, 81; 604/111, 189, 604/404
See application file for complete search history.

(56) References Cited

U.S. PATENT DOCUMENTS

| | | | | |
|---|---|---|---|---|
| 4,921,277 A * | 5/1990 | McDonough | ............. | G09F 3/00 283/100 |
| 5,225,162 A * | 7/1993 | Scoville | .................... | A61L 2/26 206/439 |
| 5,651,775 A * | 7/1997 | Walker | ............... | A61M 5/31533 604/207 |
| 6,685,678 B2 * | 2/2004 | Evans | ................. | G06F 19/3468 604/200 |
| 7,047,682 B2 * | 5/2006 | Riley | .................... | B42D 15/00 283/75 |
| 7,074,209 B2 * | 7/2006 | Evans | ................. | G06F 19/3468 235/375 |
| 7,141,286 B1 * | 11/2006 | Kessler | ............... | A61M 5/3202 206/534 |
| 7,941,949 B2 * | 5/2011 | Cloninger | ............. | G09F 3/0288 283/101 |
| 8,140,349 B2 * | 3/2012 | Hanson | ............... | A61M 5/1456 235/375 |
| 2001/0056258 A1 * | 12/2001 | Evans | ............... | A61M 5/31533 604/131 |
| 2002/0020459 A1 * | 2/2002 | Baldwin | ................ | A61M 5/28 141/11 |
| 2003/0055685 A1 * | 3/2003 | Cobb | .................... | A61M 5/172 705/3 |
| 2004/0168741 A1 | 9/2004 | Baldwin | | |
| 2008/0188814 A1 * | 8/2008 | Lavi-Loebl | ............. | A61M 5/28 604/189 |
| 2008/0243088 A1 * | 10/2008 | Evans | ............... | A61M 5/31525 604/246 |
| 2010/0024268 A1 * | 2/2010 | Landsman | .............. | G09F 3/005 40/633 |
| 2010/0036678 A1 * | 2/2010 | Bray | .................... | G06F 19/3406 705/3 |
| 2010/0097223 A1 * | 4/2010 | Kruest | ................ | E05B 47/0009 340/572.1 |
| 2011/0306072 A1 * | 12/2011 | Nicholls | ............. | B01F 13/0071 435/11 |
| 2013/0073312 A1 * | 3/2013 | Thompson | .......... | G06F 19/3462 705/2 |
| 2013/0096511 A1 * | 4/2013 | MacArthur | ................. | A61J 1/06 604/189 |
| 2013/0204202 A1 * | 8/2013 | Trombly | ............... | A61M 5/172 604/207 |

FOREIGN PATENT DOCUMENTS

| | | |
|---|---|---|
| JP | 03-124022 | 8/2006 |
| JP | 2006-285036 | 10/2006 |
| JP | 2007-190128 | 8/2007 |

OTHER PUBLICATIONS

Extended European Search Report issued in EP Patent Application No. 12890246.7 dated Aug. 2, 2016.

* cited by examiner

Fig.4
(a)
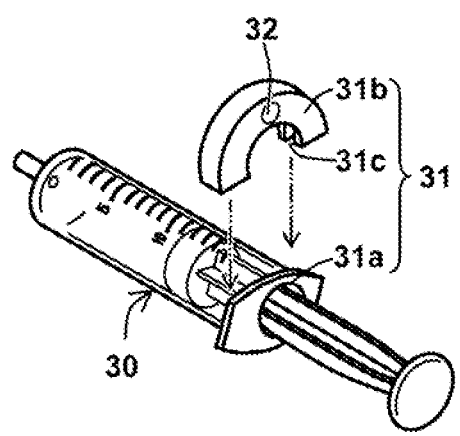
(b)
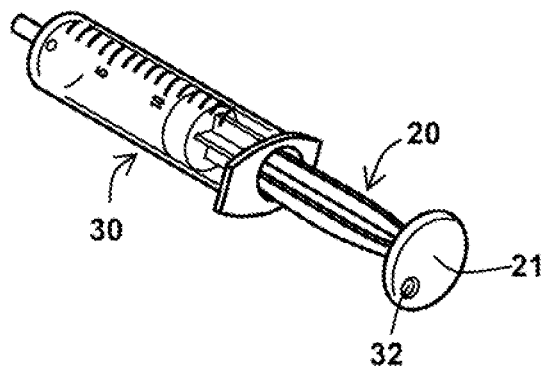

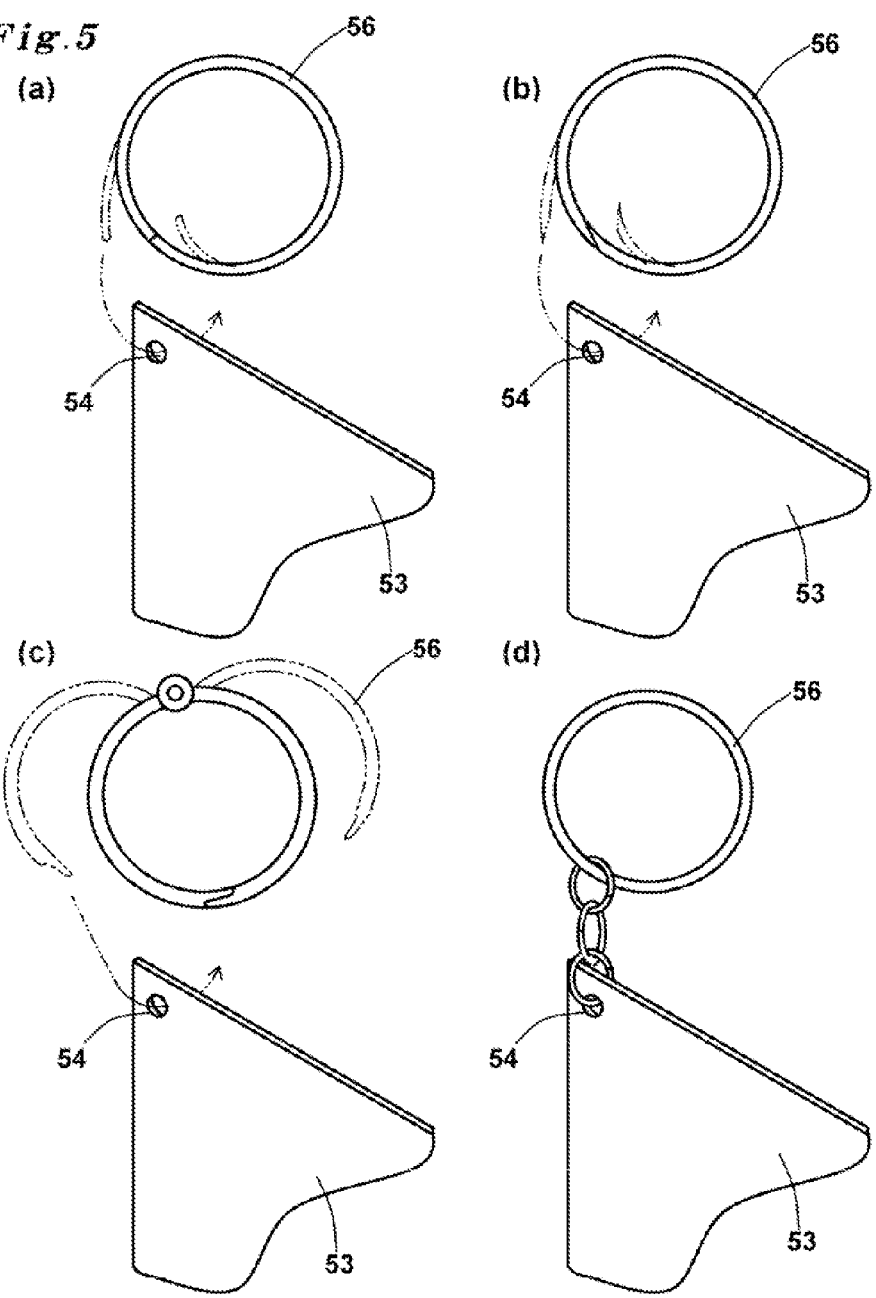

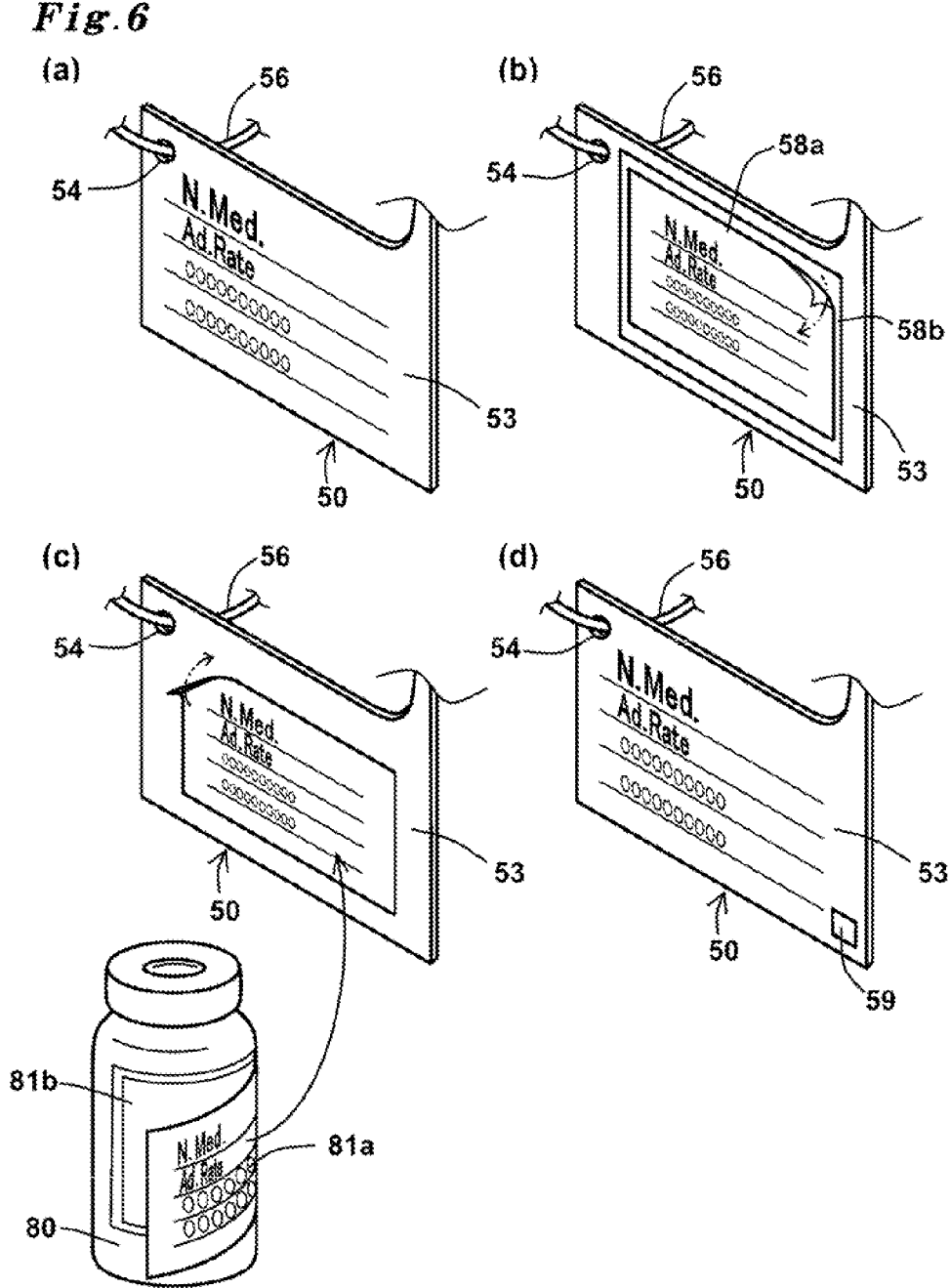

SYRINGE WITH HANGING TAG

TECHNICAL FIELD

The present invention relates to a syringe, from which a tag for indicating administration status of a medical liquid is hanged, wherein the medical liquid is gradually discharged from the syringe under a predetermined administration rate by a syringe pump in administering the medical liquid to a patient.

BACKGROUND ART

When a patient is medicated with a liquid medicament such as a narcotic, a sedative and a cardiotonic over a long time m an operating room or an intensive care unit of a hospital, the liquid medicaments are administered little by little to the patient from a syringe by using a syringe pump under a predetermined administration rate. While monitoring a patient's state or an electrocardiogram etc., medical doctors such as an operating surgeon and an anesthetist or a clinical engineer under the medical doctor's directives control the dose and an administration rate suitably so that the liquid medicament is optimally administered.

In such cases, the following medical malpractices have been reported not a little every year. For example, a medicament other than a prescription was incorrectly prepared in a syringe and administered to a patient, incorrect dosage of a prescription was administered, or incorrect drive conditions of a syringe pump were mistakenly set for dose and administration role which should be appropriate during an operation or treatment.

In medical practices, measures against such a human error, are taken. For example, medical doctors or nurses in medical practices reconfirm a label of an ampule accommodating pharmaceutical ingredients before or during preparation of a liquid medicament. And they directly fill out administration information such as a name of a medicament, a dose or a concentration thereof, and an administration rate thereof onto a syringe or a label attached thereon, before or after preparation of the liquid medicament for administration from the ampule. Furthermore, during the administration, they repeatedly check the name of the medicament, the dose thereof, the concentration thereof, the administration rate, the repetition of the administration and the integrated amount of the administration, the remained amount of the medicament etc. Thus, a number of items are checked several times so that a human error may not happen before and during the operation, and during the treatment.

Patent Document 1 discloses a medical container such as a transparent prefilled syringe as below. The medical container comprises a first volume-measurement means indicating a volume of content therein, which is provided on one side of wall portions facing each other in the medical container so as to be directly viewable, and a second volume-measurement means indicating a volume of the contents therein, which is provided on another side of the wall portions lacing each other in the medical container so as to be viewable through the one side of the wall portions. And a writable label, in which data writing parts are disposed, is stuck on the medical container.

Even if two or more of such checks are performed, there are still some of the following problems. For example, a number of the syringes set on plural syringe pumps are mutually confusing because the syringes are put in parallel in the operating room or the intensive care unit. Furthermore, if the amount of the liquid medicament to be administered such as the anesthetic etc. is small, it is hard to visually check the administration status for each syringe in one glance by the operating surgeons by the lying patient in the operating room, the anesthetist or the clinical engineer who optimize the anesthetized state near the foot of the patient, or a attending physician who treats the patient in the intensive care unit, because the syringe is too small and the administration information of terms written on the syringe or in the label thereon is too small. Moreover, when the administration information is directly written down on a syringe, the information should be written by using a pen of an oil-based ink because the syringe is made from non-polar plastics such as a cycloolefin resin and a polypropylene resin. And since the syringe is cylindrical, it is hard to write down legible and clear words of the administration information on syringe or in the label thereon. Likewise, the administration information marginally written on the syringe or in the label thereon may be visually distorted due to a bent surface of the syringe having a cylindrical shape. It is also hard to visually check the terms of the information which are unexpectedly located at an upper or lower side or a back side of the cylindrical shape of the syringe. Additionally, when the terms are written thereon, it is hard to check residual quantity of the liquid medicament because graduations disposed on a surface of the syringe may be unreadable.

Preventive actions for elimination of human errors such as error concerning use of medical appliances or medical equipments are referred to as so-called human factor engineering. The design through the human factor engineering is becoming a de facto standard for manufacture or approval requests of the medical appliances or the medical equipments. However syringes for administration by using a syringe pump have not been put into practical use according to effective human factor engineering yet.

PRIOR ART DOCUMENTS

Patent Documents

Patent Document 1: JP2007-190128A1

SUMMARY OF INVENTION

Problem to be Solved by the Invention

According to the present invention, in order to solve the above-mentioned problems, a syringe having a tag which enables to indicate administration status of a liquid medicament simply and demonstrably, can be checked by medical doctors etc. in one glance, and is hard to be misidentified, in administering a liquid medicament to a patient from the syringe by using a syringe pump.

Means for Solving Problem

A syringe with a hanging tag of the present invention in order to achieve above-mentioned objects comprises:
a pusher having a gasket at a head end thereof and a pressing portion at a base end thereof,
a syringe barrel having a nozzle at a leading end thereof and a flange on a rim of a rear end side thereof, in which the pusher is inserted such that the gasket is slidable,
a liquid medicament chamber accommodating a liquid medicament between the gasket and an outflow hole of the liquid medicament on the nozzle in the syringe barrel and, a tag for indicating administration status of the liquid medicament;

and the syringe being connectable to a syringe barrel nozzle connecting section, which is attached to a liquid medicament delivery tube, through the nozzle, the syringe former having:

an engaging hole which is provided on the flange or the pusher, an engaging section which is extended from the tag for indicating the administration status of the liquid medicament and latched to the engaging hole, and a hanger provided with the tag which passes through any one of the syringe barrel, the nozzle, the liquid medicament delivery tube and the syringe barrel nozzle connecting section, so that the tag is hanged therefrom.

The syringe with the hanging tag is used to be set on a syringe pump.

It is preferable that in the syringe with the hanging tag, a through hole is opened through the tag, and the hanger is annular and passes through the through hole.

In the syringe with the hanging tag, the engaging section may have a pawl which is latched on the engaging hole and not able to be plucked therefrom in inserting the engaging section to the engaging hole.

In the syringe with the hanging tag, the tag and the engaging section may be integrally constructed.

It is preferable that in the syringe with the hanging tag, the engaging section and the hanger are adjusted for size, length and shape so that the tag and the syringe set on a pedestal of a syringe pump are provided to be substantively parallelized.

It is further preferable that in the syringe with the hanging tag, the engaging section and the hanger are adjusted for size, length and shape so that the tag does not obstruct a graduation for indicating liquid medicament volume which is provided around the liquid medicament chamber.

In the syringe with the hanging tag, the tag provides:
a column or a space for putting any one of administration conditions of patient's name, identification number, sex, age and weight, date and time, medicament's name, dose, concentration and administration rate, points of concern, the integrated amount of administration, poisonous and deleterious pharmacopoeia, regulatory matters, and a disease name, on record, or
a space for sticking a seal written or printed any one of the administration conditions.

An indicating member for administration status of the present invention in order to achieve above-mentioned objects, is hanged from syringe comprising:
a pusher having a gasket at a head end thereof and a pressing portion at a base end thereof,
a syringe barrel having a nozzle at a leading end thereof and a flange on a rim of a rear end side thereof, in which the pusher is inserted such that the gasket is slidable, and a liquid medicament chamber accommodating a liquid medicament between the gasket and an outflow hole of the liquid medicament on the nozzle in the syringe barrel, and is connectable to a syringe barrel nozzle connecting section which is attached to a liquid medicament delivery tube through the nozzle, comprising:
a tag for indicating administration status,
an engaging section which is extended from the tag and is enabled to be latched to an engaging hole opened on the pusher or the flange of the syringe barrel, and
a hanger which passes through a through hole of the tag, and is passed through a flow path from the syringe barrel to the liquid medicament delivery tube connected thereto so that the hanger makes the tag hang.

Effect of the Invention

The syringe with the hanging tag of the present invention can be used for wide purposes in administering the liquid medicament to the patient from the syringe by using the syringe pump in the operating room or the intensive care unit. According to the syringe with the hanging tag, the administration status of the liquid medicament can be simply written on the tag for indicating the administration status of the liquid medicament or on the seal to be stuck on the tag. The latest administration status can be additionally put thereon. Therefore, the syringe is easy to use for the medical doctors, the clinical engineers or the nurses in the operating room or the intensive care unit. The syringe with the hanging tag can simply and demonstrably indicate the administration status of the liquid medicament by the tag for indicating the administration status of the liquid medicament. Thus, it is easy to visually check the administration states of the liquid medicament and it is hard to misidentify the status in one glance by the medical doctors etc. Accordingly, the medical doctors etc. can check the name of the medicament, the dose, the concentration, the administration rate, the integrated amount of administration, the residual quantity thereof and so on definitely and demonstrably, during the administration under the operation or the treatment.

The indicating member for the administration states of the present invention is simple, so it is easy to be manufactured and can be quickly attached to the indicating member to the syringe.

BRIEF DESCRIPTION OF DRAWINGS

FIG. 4 is a partial perspective view showing other embodiments of the engaging hole of the flange of the syringe barrel or the engaging hole of the pusher in the syringe with the hanging tag according to the present invention.

FIG. 5 is a partial perspective view showing other embodiments of the tag for indicating the administration status of the liquid medicament and the hanger which passes through the through hole thereof in the syringe with the hanging tag according to the present invention.

FIG. 6 is a partial perspective view showing other embodiments of the tag for indicating the administration status of the liquid medicament and the hanger which passes through the through hole thereof and is passed by any flow path from the syringe barrel to the liquid medicament delivery tube, in the syringe with the hanging tag according to the present invention.

MODE FOR CARRYING OUT THE INVENTION

Hereunder, embodiments to carry out the present invention in detail will be explained, but the scope of the present invention is not restricted by these embodiments.

Figure 1:
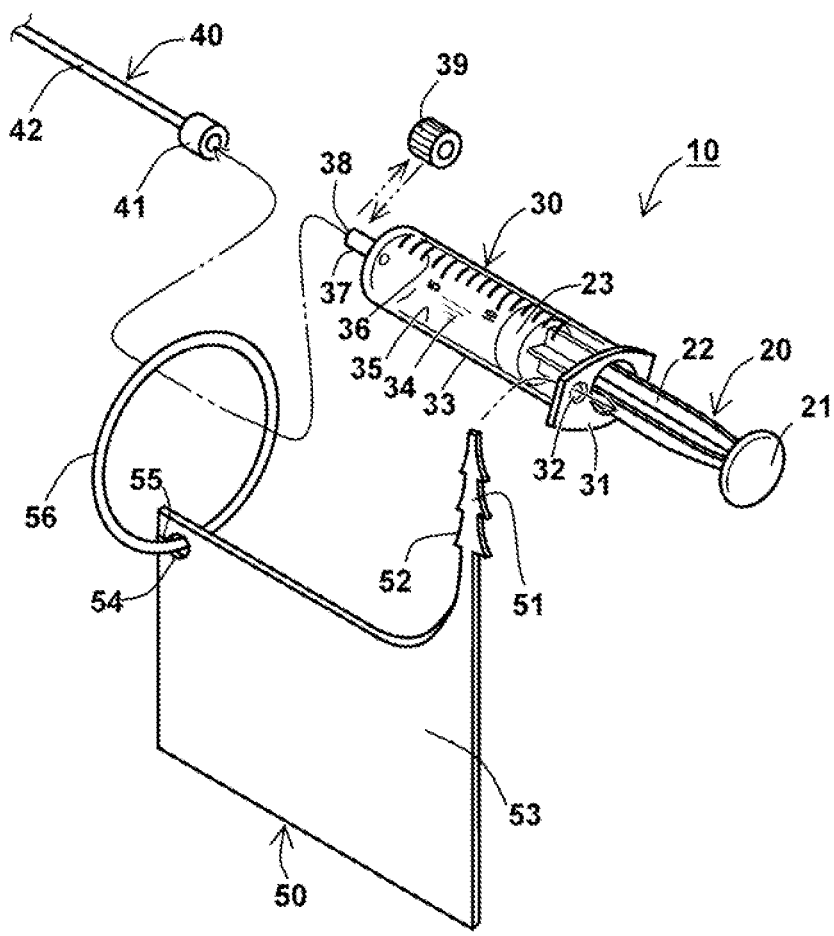
FIG. 1 is a perspective view showing an embodiment of the syringe with the hanging tag according to the present invention.

A syringe 10 with a hanging tag of a preferable embodiment of the present invention comprises a transparent syringe barrel 30 and a pusher 20 which is inserted into the syringe barrel 30, as shown in FIG. 1. An indicating member 50 for administration status, which comprises a tag 53 for indicating administration status of a liquid medicament, is hanged therefrom.

The pusher 20 has a rubber gasket 23 at a head end of a plunger 22, and a discoid pressing portion 21 at a base end of the plunger 22. As regards the plunger 22, its vertical section towards an axial direction is approximately a cross-shape. The plunger 22 is slightly slenderized on a side of the base end, and connected to the pressing portion 21. Approximately half of the plunger 22 on the side of the head end and the whole gasket 23 of the pusher 20 are inserted into a barrel portion 33 of the cylindrical syringe barrel from an aperture on a side of the base end.

A lead end portion of the syringe barrel 30 provides with a cylindrical nozzle 37 which is contracted slimly than the cylindrical barrel portion 33 thereof. The nozzle 37 has an outflow hole 38 of the liquid medicament, which makes the inside and the outside of the barrel portion 33 communicate. A liquid medicament chamber, which is circumscribed by the outflow hole 38 of the liquid medicament on the nozzle 37, the gasket 23 and an internal wall of the barrel portion 33, is provided in the barrel portion 33 of the syringe barrel 30. A liquid medicament 34 may be accommodated in the liquid medicament chamber 35. A graduation 36 for indicating liquid medicament volume, which indicates volume of the liquid medicament 34, is fitted up onto an external wall of the syringe barrel 30.

A flange 31 is expansively protruded along a perpendicular plane towards an axial direction of the syringe barrel 30 so as to surround a rim of a rear end side of the syringe barrel 30 (i.e. a periphery along an aperture of the rear end in the embodiment). The flange 31 protruded towards a major axis direction and a minor axis direction respectively, and an engaging hole 32 is bored through a major axis portion.

The indicating member 50 for the administration status possesses the rectangular tag 53 of a flat-thin unpatterned plate for indicating the administration status of the liquid medicament. The tag 53 includes an engaging section 51 at neighborhood of an upper corner thereof. The shrank engaging section 51 is provided with an extended tip portion. The engaging section 51 enables to be put into the engaging hole 32 of the flange 31 at the tip portion thereof. Neighborhood of another upper corner of the tag 53 is a fixing portion and is provided with a fitting hole 54 bored.

The indicating member 50 for the administration status is integrally formed in a manner of fashioning, punching and/or clipping of the engaging section 51, the tag 53 and the fitting hole 54.

The tag 53 is made from plastic and/or paper. It is preferable that the tag 53 is made from writable materials with a pencil or a pen of an oil-based ink or water-based ink. The tag 53 has a comfortable fill-in space for writing down administration conditions such as a patient's name, sex, or weight, date and time, a medicament's name, dose, concentration, or administration rate, points of concern, an integrated amount of administration at a predetermined time, residual quantity and so on, all which should be checked before operation, during operation or during treatment. In the tag 53, at least a portion of the engaging section 51 is flexible. And the tag 53 may be a configuration of recording paper such as a paper sheet put in a transparent cover case of a card case so as to indicate the conditions.

It is more preferable that the tag 53 consists of paper and/or plastic and has a plate-like shape.

Discriminable hues may be preliminarily defined according to medicinal active ingredients in the liquid medicament 34. Then at least any one of the tag 53, the plunger 22 and the pressing portion 21 of the pusher 20 may be colored with the hue indicating a sort of the liquid medicament 34.

The engaging section 51 has pawls 52 which are latched on and not plucked from the engaging hole 32 in inserting pawls thereto. The pawls 52 have sawtooth patterns which are provided along both side edges. Width between both tooth points of sawtooth pawls 52 projected over both side edges is slightly greater than a diameter of the engaging hole 32. When the engaging section 53 is inserted to engaging hole 32, it is wrapped and passes through the hole 32 due to comparative flexibility of the engaging section 51 and then the sawtooth pawls 52 are restored due to biasing according to the flexibility. In consequence, the pawls 52 are latched to be engaged on and not plucked from the edge of the engaging hole 32. The engaging hole 32 is a circular hole so that the engaging section 51 is inserted from any direction to the hole 32.

The fitting hole 54 provided on the fixing portion of the tag 53 comprises a notch 55 which is located along a line connected between an edge of the tag 53 and an edge of the fitting hole 54 within the shortest distance. A hanger, which is seamless, annular, rigid and hard, passes through the lifting hole 54. The hanger 56 is plunged from a slightly-openable slit (not shown) twisting the notch 55 into the fitting hole 54 to pass through the fitting hole 54.

The nozzle 37 of the syringe barrel 30 can be connected to a transfusion line 40. The nozzle 37 provided with the outflow hole 38 of the liquid medicament, which discharges the liquid medicament 34 from the syringe barrel 30 by sliding the gasket 23 according to pushing of the pressing portion 21 by a syringe pump (see FIG. 2). The nozzle 37 is connected to a liquid medicament delivery tube 42 located on a base end side of a transfusion line 40. The liquid medicament delivery tube 42 equips a syringe barrel nozzle connecting section 41 which makes the outflow hole 38 of the liquid medicament communicate to the liquid medicament delivery tube 42 by connecting the nozzle 37 of the syringe barrel 30 on a delivery terminal of a base end thereof. The syringe barrel nozzle connecting section 41 may surround the delivery terminal of the base end of the liquid medicament delivery tube 42 in order to be inserted by the nozzle 37 of the syringe barrel 30 and to screw the nozzle 37. Or the syringe barrel nozzle connecting section 41 may double as a tube terminal of the liquid medicament delivery tube 42 in order to be inserted by the nozzle 37 and to screw or put the nozzle 37.

The hanger 56 is annular. Thereby, the hanger 56 can be passes through any one of the barrel portion 33 of the syringe barrel 30, the nozzle 37, the liquid medicament delivery tube 42 and the syringe barrel nozzle connecting section 41, so that the hanger 56 can be hanged therefrom. Since the hanger 56 is passed by them to be hanged therefrom and the engaging section 51 is latched on and not plucked from the engaging hole 32, the tag 53 of the indicating member 50 for the administration status features a state where the tag 53 is hanged therefrom. The hanger 56 may be used with a tool such as a S-shape hook to fit thereon, instead of the annular one.

The syringe 10 with the hanging tag may be sterilized by a sterilization treatment of autoclave or other sterilization treatment using ethylene oxide gas, gamma ray or electron beam.

The syringe 10 with the hanging tag may be a prefillable syringe whose syringe barrel 30 is vacant, a prefilled syringe in which the liquid medicament 34 of the liquid medicament chamber 35 is preliminarily accommodated, or a vacant syringe which sucks the liquid medicament which is encapsulated in a capsule (not shown) of medicinal active ingredients or which is prepared by solving solid ingredients when used. The nozzle 37 of the syringe barrel 30 is sealed by an interchangeable cap 39.

The medicinal active ingredients of the liquid medicament 34 are exemplified with an anesthetic agent such as propofol of a $GABA_A$ receptor agonist; an analgetic agent such as an opioid antagonist of a narcotic agent; a cardiac or vasopressor agent such as a catecholamine derivative; a vasodilator agent such as a nitrate agent; a depressor agent such as a calcium antagonist; a muscular relaxant; an antibiotic agent; a parasympatholytic agent; a carcinosiatic or chemotherapeutic agent; an antiarrhythmic agent such as lidocaine; an anticonvulsant agent; a bronchodilator agent; a potassium preparation such as potassium chloride; an insulin preparation; an antibody preparation; an antirheumatic agent; and a contrast medium such as a gadolinium preparation.

Since thus liquid medicament 34 is accommodated in a tiny amount of equal or less than 20 ml for example 0.5-20 ml, especially 0.5-10 ml as an insubstantial administration amount in the liquid medicament chamber 35 of the syringe 10 with the hanging tag, the syringe barrel 30 has a thin external diameter of about 5-30 mm and short tube length of about 50-100 mm. Because the tag 53 written with the administration status of the liquid medicament is hanged according to the syringe 10 with the hanging tag, the name of medicament and the administration rate etc are clear to be shown and easy to be confirmed much more than ones on a syringe barrel written with the administration status directly.

Even if the syringe 10 with the hanging tag is a syringe which accommodates a large amount specifically 20-100 ml of the liquid medicament, the hanging tag 53 is used for the human factor engineering because of a purpose for completely writing the information of the administration conditions being written down in the tag 53 when the every information is multiple and is hard to be written down, or another purpose for standardizing a indicating manner of the written information such as the administration conditions for other medical devices such as syringes.

Specifically, if the syringe 10 with the hanging tag is put on the syringe pump, the syringe for a small amount is effective to use for capacity of at maximum 20 ml in the liquid medicament chamber.

The syringe 10 with the hanging tag is manufactured as below.

First of all, the tag 53 for indicating administration status of the liquid medicament and the engaging section 51 having the pawls 52 of the sawtooth patterns are punched together from a sheet made of plastic and/or paper or a sheet coated with a protective plastic film. The a fitting hole 54 is punched by a prick punch etc. on the fixing portion located nearby another side of the engaging section 51 of the tag 53, and then the notch 55 is provided by a cutter. The annular hanger 56 is plunged from notch 55 to prepare the indicating member 50 for the administration status.

The engaging section 51 of the indicating member 50 for the administration status with the pawls 52 having a shrank top portion is flipped and put into the engaging hole 32 on the flange 31 of the syringe barrel 30 and is inserted therethrough until the pawl 53 climbs over the engaging hole 32. The engaging section 51 is latched to engage the engaging hole 32 by the pawls 52, finally the syringe with the banging tag is manufactured.

Hereafter, a method for using the syringe 10 with the hanging tag is explained with reference to FIG. 2.

The syringe 10 with the hanging tag is explained as an exemplified embodiment for preparing the liquid medicament 34 when used. A nurse or a medical doctor readies an ampule accommodating pharmaceutical ingredients based on a prescription. A solution for dilution such as a saline solution is added thereto according to the prescription to prepare the liquid medicament having a desired concentration. The cap 39 is uncoupled from the syringe 10 with the hanging tag, and interchanged to a needle having a hub if necessary, and the liquid medicament in the ampule is socked by pulling up the pusher 20. If desired, the nozzle 37 of the syringe 10 is upturned and the pusher 20 is nudged to remove discarded residual air bubbles. The syringe 10 with the hanging tag is completely prepared for administration.

Necessary information such as administration conditions illustrated with a patient's name, an identification, number, sex, age, weight, date and time, a name of a medicament (abbr. N. Med.), a dose, a concentration, an administration rate (abbr. Ad. Rate), points of concern, an integrated amount of administration (abbr. Intg. Ad.), poisonous and deleterious pharmacopoeia, regulatory matters or a disease name, or an attending doctor is preliminary written on the tag 53 by a pencil or a pen of an oil-based ink or water-based ink. Size of written characters just has to be appropriate so that the anesthetist etc. standing at some distance from the patient can demonstrably watch them. However, the size is at least about 8 points such that the doctors can clearly have a look at them in checking thereof repeatedly. It is conscientiously checked whether the liquid medicament 34 is adequately prepared in the syringe 10 with the hanging tag or the administration conditions are exactly written according to doctor's instructions or prescriptions.

When the nozzle 37 of the syringe 10 with the hanging tag is connected to the syringe barrel nozzle connecting section 41 of the liquid medicament delivery tube 42 on the delivery terminal of the base end of the transfusion line 40, they are passed through the hanger 56. The syringe 10 with the hanging tag is set on the syringe pump. The hanger 56 of the syringe 10 with the hanging tag is passed by any flow path from the barrel portion 33 of the syringe barrel 30, the nozzle 37, the syringe barrel nozzle connecting section 41, and the liquid medicament delivery tube 42 to be hanged. The engaging section 51 is latched on and not plucked from the engaging hole 32 provided on the syringe barrel 30. The tag 53 of the indicating member 50 for the administration status is used as holding a hanging state.

The doctors etc. reconfirm the administration status on the tag 53. The syringe pump 60 is driven according to the written information of the administration status of the liquid medicament. After a main switch 68 is turned on and lighting of an AC-charge indication lamp is checked, the syringe pump is prepared to be completed.

The flange 31 of the syringe barrel 30 is set into pedestal-slits 75. The syringe 10 is fixed not to be moved over thereby in driving the syringe pump 60. The pressing portion 21 of the pusher 20 is set in between slider hooks 71 which are provided on a slider 70 for pushing the pusher 20. A clutch lever 72, which can let in or throw out a clutch of the slider 70, is folded forward to clamp the pressing portion 21 on the slider 70. And then, a syringe clamp 74 is folded forward until touching to the syringe 10 so as to hold the syringe 10. An inclination angle of the syringe clamp 74 is detected to be converted into a syringe size. After those procedures, the syringe 10 with the hanging tag is set on a sagged pedestal 76 with a curved groove to be mounted.

In this occasion, the engaging section 51 is gravitationally bended and the tag 53 of the indicating member 50 for the administration status is suspended below the pedestal 76 of the syringe pump 60. Furthermore the hanger 56 is leaned over the pedestal 76 of the syringe pump and hangs the tag 53. Thereby the tag 53 of the indicating member 50 for the administration status is suspended along the pedestal 76 almost parallel. Then the tag 53 is suspended in front of the syringe pump 60 so that the medical doctors can easily check it without encumbering operation of a console panel on the syringe pump 60 and without hiding the graduation 36 for indicating liquid medicament volume on the syringe barrel 30.

Herewith, the indicating member 50 is put oneself into a state in which the tag 53 does not incline. Therefore the administration status information written down on the tag 53 is unobstructed from any positions where the doctors work so as to be easily confirmed. And when the tag 53 is suspended to be hanged, the residual quantity of the liquid medicament is easy to be monitored because the graduation 36 for indicating liquid medicament volume is not hidden by the tag 53.

Display-changeover switches 61 makes adjustment matters such as a flow rate or integrated amount of administration of the liquid medicament etc. indicate on a display panel 63. The adjustment matters are regulated as appropriate values based on the size of the syringe according to the administration conditions written on the tag 53 by using setting switches 62 of +/− buttons. When a fast-forwarding switch 65 is flipped on to drive an incorporated motor (not shown), a transmission drive 73 of the slider screwed with the slider 70 rotates. The slider 70 moves in a direction indicated by an arrow thereby in order to push the pusher 20. After the liquid medicament makes a residual air expel from a terminal (not shown) of the liquid medicament delivery tube 42 to be filled therein, the fast-forwarding switch 65 is turned off. Then, the terminal of the liquid medicament delivery tube 42 is directly connected to an indwelling needle puncturing to a vein of the patient, or is connected to a three-way stopcock or infusion bag of the transfusion line 40 which connects to an indwelling needle puncturing to a vein of the patient.

The administration status of the liquid medicament written on the tag 53 is checked again. When the setting conditions are correct, the administration thereof is started. A start/stop switch 66 is flipped on to drive the incorporated motor for moving the slider 70. Thereby, the pusher 20 is started to be pushed so that the liquid medicament 34 is discharged according to the previously determined flow rate. Lighting of an operation indicator 69 is checked, also extinction of an alarm lamp 64 which warns an abnormal circumstance is checked. While conditions of the patient and an electrocardiogram etc. are monitored, actual administration status and the predetermined administration conditions written on the tag 53 are timely checked.

Since the legible characters with appropriate size are written on the tag 53, the doctors etc. do not misread the administration status written thereon. If necessary, they may rewrite or insert additional matters such as a setting-changed flow rate, an integrated amount of administration, time when checking etc. on the tag 53. The doctors etc. check the actual administration status and the predetermined administration conditions written on the tag 53 are iteratively checked during the operation or the treatment. Thus, checking a number of matters of them over again and again before/during the operation or during the treatment prevents from human errors.

When the administration has been unnecessary after the operation or during the treatment, the start/stop switch 66 of the syringe pump 60 is turned off to stop the drive thereof for discontinuing the administration.

Finally, the syringe 10 with the hanging tag is discarded with the transfusion line 40, as clinical wastes.

The clinical wastes written with personal information such as a name of a patient would be often treated with eliding characters thereof or hashing them. Thus treatments are troublesome and involve risks of infection or injury. However, when the information is exclusively written on a tag, a portion written the information may be entirely cut out to hash it by a shredder easily. Thereby countermeasure for leaking the information is provided safely and certainly.

After cutting it off, the tag 53 may be stored as medical history in oneself. After a process such as photography or digital scanning of the tag 53, it may be used on an electronic hospital chart. On a paper hospital chart, the pasted tag 53 may be stuck by re-labeling or the written portion cut from the tag 53 may be starched up. If the detail information is rounded up on the tag in those instances, the information is easy to be stored and is legible for reconfirmation thereof.

Figure 2:
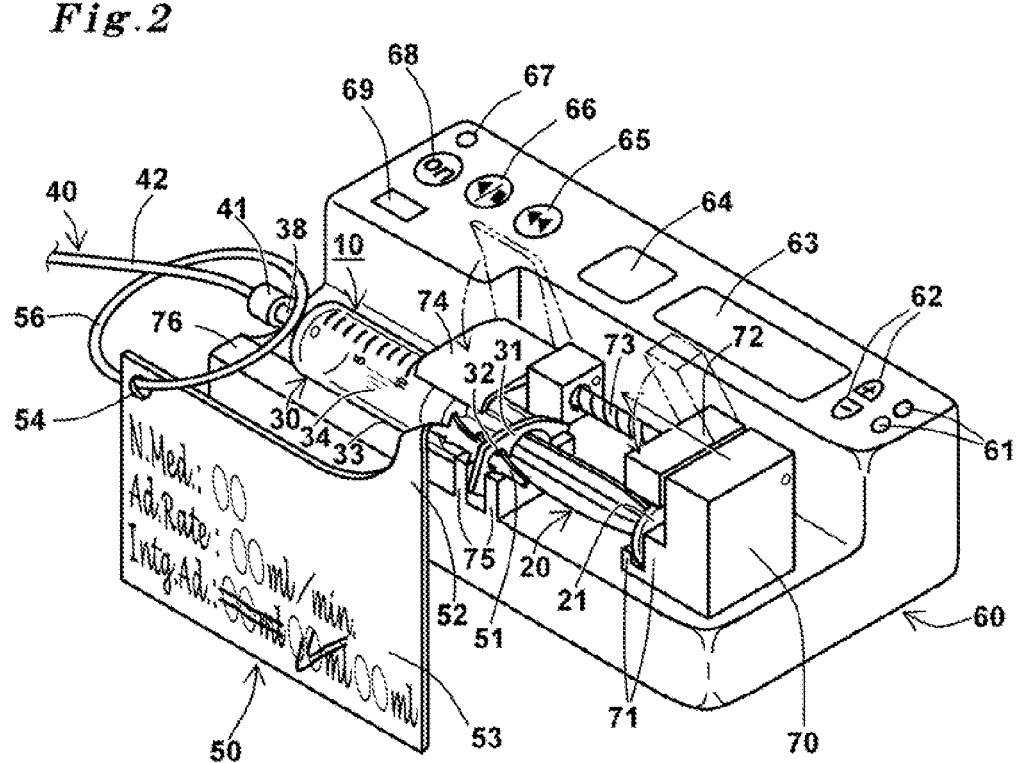
FIG. 2 is a perspective view showing a situation of using the syringe with the hanging tag according to the present invention.

As heretofore described, the preferable embodiment of the syringe 10 with the hanging tag is explained referring to FIGS. 1 and 2. However, features of the syringe 10 with the hanging tag may be modified within the scope of the present invention.

Figure 3:
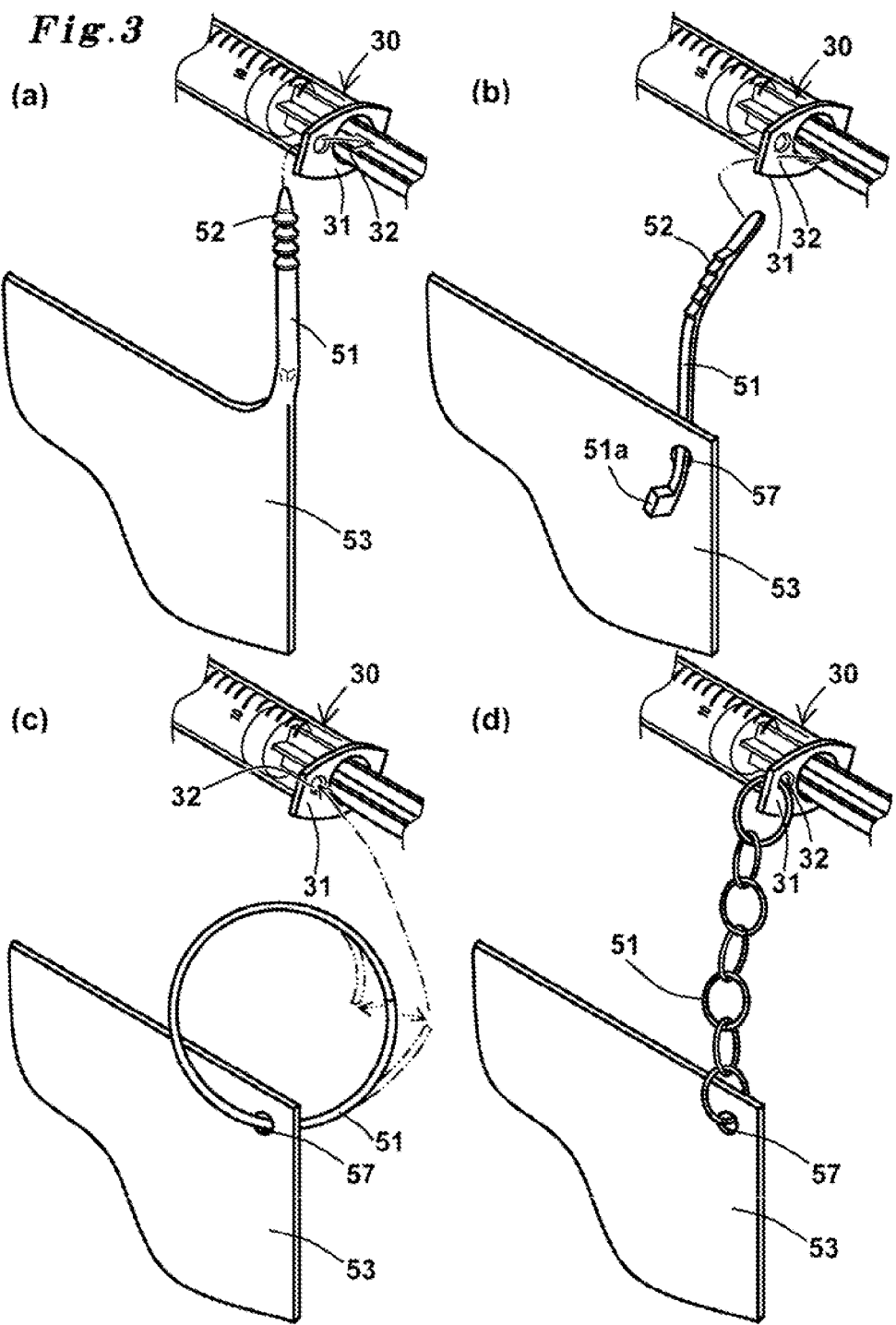
FIG. 3 is a partial perspective view showing other embodiments of the tag for indicating the administration status of the liquid medicament and the engaging section being to be latched with the engaging hole in the syringe with the hanging tag.

As shown FIG. 3, an engaging section 51, which latches an engaging hole 32 on a flange 31 of a syringe barrel 30, may be varied in an adequate shape.

It is preferable that an engaging section 51 has pawls 52, which are latched on an engaging hole 32 and not able to be plucked therefrom in inserting it to the engaging hole 32, because the tag cannot be replaced after latching thereto, and therefore other tag 53 will not be mistakenly attached. For example, as shown in FIG. 3 (*a*), an engaging section 51 may have a substantively-cylindrical shape which extends from one corner of a tabular tag 53, and be provided with multiple conical pawls 52 along it. The multiple conical pawls 52 prevent to be plucked therefrom though multistep-latching thereof. And the engaging section 51 is not irreversibly plucked therefrom, because the engaging section 51 is inserted along an insertion direction and is not backed forward due to a large contact area between the conical pawls 52 and edge of the engaging hole 32. As shown in FIG. 3 (*b*), an engaging section 51 may be a belt-shape band having saw-tooth pawls 52 which are provided on one or both lateral side around one terminal thereof and are irreversibly latched to an engaging hole 32, and a bump 51*a* of an engaging section which is provided around other terminal thereof and is latched to a through hole 57 punched on a tag 53 due to being larger than the hole 57. An engaging section 51 may be a so-called binding band having saw-tooth engaging pawls which are provided on one lateral side around one terminal thereof, and a buckle having a latch projection which is provided around other terminal thereof and enables to run over the engaging pawls along a fastening direction and enables to latch the engaging pawls forward in order to lock annularly by binding (not shown).

Alternatively, if an engaging section 51 is not able to be plucked from an engaging hole 32 without a pawl 52, a tag 53 cannot be replaced after latching thereto, and therefore other tag will not be mistakenly attached. For example, as shown in FIG. 3 (*c*), an engaging section 51 may be a practically-hard and slightly-flexible circular ring having a break split up, which is purposely distorted by an external force. The engaging section 51 suspends a tag 53 by distorting it at both terminals of the break of the ring and then passing through an engaging hole 32 on a flange 31 of a syringe barrel 30 and a through hole 57 of the tag 53. The break may be perpendicular to a circular arc of the ring as shown in the figure, and may be inclined against a circular arc of the ring as not shown in the figures. And as shown in FIG. 3 (d), a tag 53 is suspended by chaining an engaging hole 32 on a flange 31 of a syringe barrel 30 to a through hole 57 of the tag 53 through a engaging section 51 of a chain.

An engaging hole 32 on a flange 31 of a syringe barrel 30 may be a circular hole, a polygonal hole such as a square hole, in shape. Although embodiment of the engaging hole 32 provided on the flange 31 expanding from a circumference around an aperture on a base end side of the syringe barrel 30 outward is illustrated, an engaging hole 32 may be provided on an attaching flange 31b which insets into a flange 31a (see FIG. 1) on a base end side of a syringe barrel 30 to expand an external diameter as shown in FIG. 4 (a). Concretely the flanges 31 compose the contracting flange 31a which surrounds the syringe barrel 30, and the attaching flange 31b which expand the external diameter of the contracting flange 31a, and a slit 31c for insetting a flange which is provided inside the attaching flange 31b to sandwich the contracting flange 31a. And the engaging hole 32 is provided on the attaching flange 31b. As shown in FIG. 4 (b), an engaging hole 32 may be provided on a pressing portion 21 of a pusher 20. In this case, while the pusher 20 is pushed, a hanger 56 with a tag 53 moves inevitably. Accordingly the hanger 56 is passed by and suspended on a seamless liquid medicament delivery tube 42 such that the hanger 56 is prevented from encumbering a slide motion thereof due to hooking anywhere on a barrel portion 33 of a syringe barrel 30, a nozzle 37, a syringe barrel nozzle connecting section 41 and a liquid medicament delivery tube 42 (see FIG. 1)

As shown in FIG. 5, a shape of a hanger 56 passed through a fitting hole 54 of a tag 53 may adequately be modified.

For example, as shown in FIG. 5 (a), a hanger 56 may be a practically-hard and slightly-flexible circular ring having a break split up, which is purposely distorted by an external force. The hanger 56 suspends a tag 53 by distorting it at both terminals of the break of the ring and then passing through a fitting hole 54 of the tag 53. The break may be perpendicular to the circular ring as shown in FIG. 5 (a), and may be inclined against the circular ring not to be able to be plucked therefrom as not shown in FIG. 5(b). A ring may have a screw joint for thread-lasting of a break (not shown). Or as shown in FIG. 5 (c), a hanger 56 may be a so-called card ring which composes semicircular pegs which are pivotally supported. A hanger 56 may be a chain hitching a terminal large-diameter ring as shown in FIG. 5 (d). A hanger 51 may be an elastic band, a ligature, or a binding band for binding itself circularly as mentioned above (not shown). A hanger may be composed by combining any of them.

As regards a tag 53 and an engaging section 51, shape, material for writing the conditions, or matters being written, may be appropriately modified as shown in FIG. 6.

It is necessary that the tag 53 has adequate size so that the doctors etc. can easily watch it at approximately 5 m away in the operating room or intensive care unit. The tag 53 has the size of length of 2 cm or more and width of 5 cm or more, especially length of 3 cm or more and width of 7 cm or more.

It is furthermore preferable that the administration status of the liquid medicament is written in several lines thereon.

The unused tag 53 may be blank such that desired administration status of the liquid medicament can be arbitrarily written, as shown in FIGS. 1 and 2. The tag 53 may have entry columns for preliminarily writing characters and values of the matters of the administration status of the liquid medicament such as a corresponding value of an amount of administration and a threshold limit of an integrated amount of administration, besides "a name of medicament" of an ingredient or a tradename of the liquid medicament 34 or "an administration dosage" of dose, concentration or rate of administration as shown in FIG. 6(a). A tag 53 may have a releasable and stickable seal 58a printing matters of administration status of a liquid medicament with entry columns for them on an upper side thereof and attaching an adhesive layer on an under side thereof, and a release layer 58b, as shown in FIG. 6(b). The seal 58 as a clinical record can be stuck on a hospital chart after using the syringe 10 with the hanging tag. A tag 53 may have a re-stuck label seal 81a from an ampule 80, around which the seal 81a is attached though a release layer 81b in order to sticking and then releasing thereof as shown in FIG. 6 (c). It is preferable that the label seal 81a is printed with matters of administration status of a liquid medicament with entry columns for them. A tag 53 may comprise printed matters of administration status of a liquid medicament with entry columns for them, and a contact-free writable/readable integrated circuit chip 59 recorded data of them, as shown in FIG. 6 (d). The integrated circuit chip 59 can be stored as a medical record with a hospital chart after using the syringe 10 with the hanging tag.

Materials of the tag 53 and the engaging section 51 are not intended to be limited as long as plastic and/or paper. Examples of the plastic materials are flexible polyvinyl chloride, polypropylene, polyethylene, ethylene-propylene copolymer, ethylene-propylene-diene copolymer, ethylene-vinyl acetate copolymer, ethylene-vinyl alcohol copolymer, poly(4-methyl pentene-1), polybutene-1, polybutadiene, polyacrylonitrile, polystyrene, acrylonitrile-butadiene-styrene copolymer, acrylic resin, polyoxymethyl, polycarbonate, polyamide, polyimide, polyamideimide, polyester (ex. polyethylene telephthalate, polybutylene terephthalate), polysulfone, polyether ether ketone, polyether sulfone, polyaryl ether sulfone, polyphenylene sulfide, thermoplastic elastomer, polytetrafluoroethylene, ethytene-tetrafluoroethylene copolymer, polyvinylidene fluoride, and polyurethane. Examples of the paper materials are pure paper, art paper, coated paper, cast-coated paper, cellulose fiber paper, and paperboard thereof. Examples of paper made from the plastic as main materials or paper interlaced with the plastic are artificial paper, paper impregnated with synthetic resin, paper impregnated with synthetic rubber latex, paper with internal synthetic resin, and paper coated with a plastic protection film. Among them, the artificial paper made from polypropylene as main material, especially YUPO which is available from Yupo Corporation and is a registered trademark.

Examples of materials of the hanger 56 are above-mentioned plastic, natural rubber, isoprene rubber, and butylene rubber.

Materials of the syringe barrel 30, the plunger 22 or the pressing portion 21 of the pusher 20 are chosen according to points of chemical resistance, gas and fungus barrier properties and safety for living bodies etc. Examples of them are polyolefin resin such as polyethylene, polypropylene, and cyclic polyolefin; polystyrene; polycarbonate; polyester such as polyethylene telephthalate; or polyamide. Especially, when the syringe 10 is treated with sterilization by an autoclave, it is preferable that the materials thereof are resins having high heat resistance, for example polypropylene or polycarbonate. And materials of the syringe barrel 30 is preferably a cyclic olefin homopolymer or a cyclic olefin copolymer which is a resin having high transparence property which achieves to watch the liquid medicament 34 accommodated in the syringe barrel from outside, and little interaction properties to the liquid medicament 34. They are formed by molding. Examples of methods for molding are an injection molding method, a blow molding method, and a thermomolding method. Among them, the injection molding method is preferable.

Materials of the gasket 30 are chosen according to points as same as ones of the syringe barrel 30 etc. Materials include a thermoplastic elastomer such as an olefinic elastomer, a polyurethane elastomer, a polyester elastomer, a polyamide elastomer, a styrene elastomer; a rubber material such as natural rubber, isoprene rubber, butadiene rubber, styrene-butadiene rubber, silicone rubber.

The syringe 10 with the hanging tag and the indicating member 50 for the administration status for using of the tag 53 are able to indicate the administration status.

INDUSTRIAL APPLICABILITY

The syringe with the hanging tag of the present invention is used when the liquid medicament is administrated from the syringe to the patient by using the syringe pump.

EXPLANATIONS OF LETTERS OR NUMERALS

10: syringe with hanging tag, 20: pusher, 21: pressing portion, 22: plunger, 23: gasket, 30: syringe barrel, 31: flange; 31a: contracting flange, 31b: attaching flange, 31c: slit for insetting flange, 32: engaging hole, 33: barrel portion, 34: liquid medicament, 35: liquid medicament chamber, 36: graduation for indicating liquid medicament volume, 37: nozzle, 38: outflow hole of liquid medicament, 39: cap, 40; transfusion line, 41: syringe barrel nozzle connecting section, 42: liquid medicament delivery tube, 50: indicating member for administration status, 51; engaging section, 51a: bump of engaging section, 52: pawl, 53: tag, 54: fitting hole, 55: notch, 56: hanger, 57: through hole, 58a: seal, 58b: release layer, 59: integrated circuit chip, 60: syringe pump, 61: display-changeover switch, 62: setting switch, 63; display panel, 64: alarm lamp, 65: fast-forwarding switch, 66: start/stop switch, 67: AC-charge indication lamp, 68; main switch, 69; operation indicator, 70: slider, 71: slider hooks, 72; clutch lever, 73: transmission drive of slider, 74; syringe clamp, 75; pedestal-slits, 76: pedestal, 80: ampule, 81a: label seal, 81b: release layer.

What is claimed is:

1. An assembly comprising:
   a syringe comprising:
      a syringe barrel comprising a nozzle at a leading end thereof and a flange on a rim of a rear end side thereof, the nozzle having an outflow hole,
      a pusher comprising a gasket at a head end thereof and a pressing portion at a base end thereof, wherein the pusher is located in the syringe barrel such that the gasket is slidable in the syringe barrel,
      a liquid medicament chamber configured to accommodate a liquid medicament, the liquid medicament chamber being in the syringe barrel and extending between the gasket and the outflow hole of the nozzle, and
   wherein the nozzle of the syringe is connectable to a syringe barrel nozzle connecting section of a liquid medicament delivery tube,
   wherein the syringe further comprises an engaging hole located on the flange or the pusher,
   wherein the assembly further comprises an indicating member that includes:
      a tag for indicating at least one administration condition of the liquid medicament,
      an engaging section extending from the tag and attached to the syringe via the engaging hole on the flange or the pusher, and
      a hanger that is provided with the tag and configured to extend around and thereby hang from at least one of: (i) the syringe barrel, (ii) the nozzle, (iii) the liquid medicament delivery tube, and (iv) the syringe barrel nozzle connecting section,
   wherein the engaging section and the hanger are configured such that, when the syringe is inserted into a syringe pump, and the indicating member is attached to the syringe, a longitudinal direction of the tag is parallel to a longitudinal direction of the syringe,
   wherein the syringe barrel includes a graduation configured to indicate a volume of liquid medicament in the liquid medicament chamber, and
   wherein the engaging section and the hanger are configured such that, when the indicating member is attached to the syringe, the tag does not obstruct the graduation.

2. The assembly according to claim 1, wherein the syringe is configured to be inserted into a syringe pump.

3. The assembly according to claim 1, wherein the tag includes a through hole, and the hanger is attached to the tab via the through hole.

4. The assembly according to claim 1, wherein the engaging section comprises a tooth configured to latch upon insertion of the engaging section into the engaging hole such as to inhibit removal of the engaging section from the engaging hole after insertion.

5. The assembly according to claim 1, wherein the tag and the engaging section are integrally constructed.

6. The assembly according to claim 1, wherein the tag includes:
   a column or a space for recording one or more of the following administration conditions: patient's name, patient's identification number, patient's sex, patient's age, patient's weight, date, time, medicament's name, medicament's dose, medicament's concentration, medicament's administration rate, points of concern, the integrated amount of administration, poisonous and deleterious pharmacopoeia, regulatory matters, a disease name, on record, or
   a space for sticking a seal written or printed with one or more of said administration conditions.

7. The assembly according to claim 1, wherein the hanger has an annular shape.

* * * * *